(12) United States Patent
Yamazaki et al.

(10) Patent No.: US 8,827,675 B2
(45) Date of Patent: Sep. 9, 2014

(54) MOLD FOR INSERT MOLDING

(75) Inventors: Minoru Yamazaki, Nagano (JP); Tetsuo Kurasawa, Nagano (JP)

(73) Assignee: Nissei Plastic Industrial Co., Ltd. (JP)

( * ) Notice: Subject to any disclaimer, the term of this patent is extended or adjusted under 35 U.S.C. 154(b) by 257 days.

(21) Appl. No.: 13/433,425

(22) Filed: Mar. 29, 2012

(65) Prior Publication Data

US 2012/0251646 A1 Oct. 4, 2012

(30) Foreign Application Priority Data

Mar. 30, 2011 (JP) ................................ 2011-076666

(51) Int. Cl.
*B29C 45/14* (2006.01)
*B29C 45/76* (2006.01)
*A61B 5/15* (2006.01)

(52) U.S. Cl.
USPC ........................................................ 425/110

(58) Field of Classification Search
CPC ........... B29C 45/14065; B29C 45/768; A61B 5/150282; A61B 5/150618
USPC ...................... 264/275, 271.1; 425/110, 129.1
See application file for complete search history.

(56) References Cited

U.S. PATENT DOCUMENTS 3,358,689 A * 12/1967 Higgins ........................ 606/181

FOREIGN PATENT DOCUMENTS

| JP | 2005031069 | 2/2005 |
| JP | 2010148694 | 7/2010 |

* cited by examiner

*Primary Examiner* — Alison Hindenlang
(74) *Attorney, Agent, or Firm* — Adams & Wilks (57) ABSTRACT

A mold assembly includes a product cavity for producing an insert-molded product and a projection-forming cavity for, if an insert of the product is irregularly deformed or disposed in wrong orientation, forming a projection on the insert-molded product. The projection, if present on the product, blocks most of the light emitted from a light-emitting element. A photodetector detects the intensity of the received light and when the detected light intensity is less than a predetermined value due to the presence of the projection, the product is judged to be rejected. Visual inspection or optical sensors judge the product to be rejected if the product has a through-hole closed and to be acceptable if the through-hole of the product is open. This judgment does not require an X-ray inspection device or radiologists.

2 Claims, 12 Drawing Sheets

MOLD FOR INSERT MOLDING

FIELD OF THE INVENTION

The present invention relates to a mold for insert molding, in particular for producing an insert-molded puncture device for blood collection.

BACKGROUND OF THE INVENTION

Medical developments make it possible to obtain a variety of medical data from one drop of blood. The one drop of blood is sampled using a puncture device called a lancet. The puncture device may have various shapes. One exemplary puncture device is disclosed in JP 2010-148694.

Figure 22:
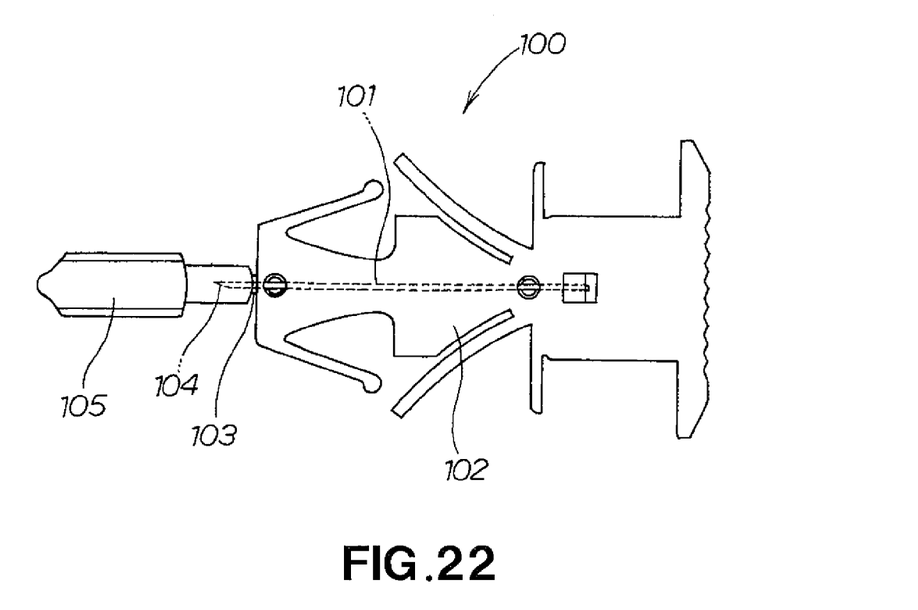
FIG. 22 is a view showing a conventional puncture device.

The puncture device disclosed in JP 2010-A-148694 will be discussed with reference to FIG. 22 hereof.

The puncture device designated at 100 includes a blood collection needle 101 having a pointed tip 104. The needle 101 has portions other than the tip which are encapsulated by a holder portion 102 of the device 100. The tip 104 of the needle 101 is encapsulated by a cap portion 105 of the device 100. The device 100 includes a neck portion 103 interconnecting the holder portion 102 and the cap portion 105. The holder portion 102, the neck portion 103 and the cap portion 105 are integral with one another. The needle 101 is made of metal. The holder portion 102, the neck portion 103 and the cap portion 105 are made from resin.

The puncture device 100 is manufactured by insert molding. More specifically, molten resin is injected into a cavity of a mold with the needle 101 set in the cavity, such that the needle 101 is encapsulated by the holder portion 102, the neck portion 103 and the cap portion 105.

The cap portion 105 covers the pointed tip 104 to ensure safe distribution of the device 100 before the device 100 is used. The cap portion 105 is twisted off breaking the neck portion 103 to expose the tip 104 of the needle 101 for use.

The needle 101 remains embedded in the resin with the tip 104 invisible until the cap portion 105 is twisted off. It is thus not possible to visually confirm whether the tip 104 is appropriately disposed pointing toward the cap portion 105. It is difficult to visually confirm whether the needle 101 exists in the resin.

To address those problems, manufactures employ an X-ray inspection to see through a completed product. This X-ray inspection has been prevalent in the art. The X-ray inspection is performed using an X-ray inspection device as taught in JP-A-2005-31069.

However, the X-ray inspection device is expensive and can be appropriately handled only by radiologists. This would result in increasing the inspection cost.

The needle 101 has such a small outer diameter, 0.3 mm to 0.5 mm that an additional device such as a magnifier is required to confirm orientation of the tip 104 of the needle 101. This also causes increase in the inspection cost.

There is a demand for a technique enabling an inspection cheaper than the X-ray inspection.

SUMMARY OF THE INVENTION

It is an object of the present invention to provide a technique enabling an easy inspection of an insert-molded product such as a puncture device.

According to one aspect of the present invention, there is provided a mold for insert molding, the mold having a product cavity configured such that molten resin is injected into the product cavity with a bar-shaped insert set in the product cavity so as to produce an insert-molded product including a resin and the insert encapsulated by the resin, the insert has a pointed end and an end opposite the pointed end, the opposite end of the insert having an end face lying in a plane perpendicular to an axis of the product, the mold comprising: an upper mold; a lower mold; and a pair of columns including an upper column integral with or releasably attached to the upper mold and a lower column integral with or releasably attached to the lower mold, the upper column and the lower column projecting into the product cavity toward the opposite end of the insert, the upper column and the lower column being configured to form a through-hole extending through the insert-molded product in a direction perpendicular to an axis of the insert, the pair of columns including: a recessed portion for receiving the opposite end of the insert, the recessed portion having a back wall for abutting on the end face of the opposite end of the insert received in the recessed portion; a resin passage portion extending through the back wall and having a cross-sectional area smaller than a cross-sectional area of the recessed portion; and a projection-forming cavity portion communicating with an outlet port of the resin passage portion for providing the insert-molded product with a projection, the projection-forming cavity portion including a surface extending perpendicularly to an axis of the through-hole and having an area larger than the cross-sectional area of the resin passage portion.

The upper and lower columns of the upper and lower molds project into the product cavity and designed to form the through-hole extending through the insert-molded product. The upper and lower columns define the recessed portion for receiving the opposite end of the insert, and the resin passage portion extending through the back wall of the recessed portion, and the projection-forming cavity portion communicating the outlet port of the resin passage portion.

If an insert-molded product has the through-hole partially closed by a projection resulting from resin filling the projection-forming cavity portion, such a product is deemed to be rejected. If an insert-molded product has the through-hole opened due to no resin filling the projection-forming cavity portion, such a product is deemed acceptable.

Visual inspection or use of optical sensors can judge an insert-molded product to be rejected if the through-hole of the product is closed by a projection and to be acceptable if the through-hole is opened. That is, the visual inspection or use of the optical sensors can inspect the insert-molded product without requiring any X-ray inspection device and radiologists. The mold according to the present invention allows visual inspection or use of the optical sensors for easy inspection of an insert-molded product.

Preferably, the insert is a blood collection needle. Although the blood collection needle is difficult to inspect because it is narrow, the mold of the present invention enables inspecting the blood collection needle at a reduced cost.

BRIEF DESCRIPTION OF THE DRAWINGS

Preferred embodiments of the present invention will be described in detail below, by way of example only, with reference to the accompanying drawings, in which.

DETAILED DESCRIPTION OF THE PREFERRED EMBODIMENT

Figure 1:
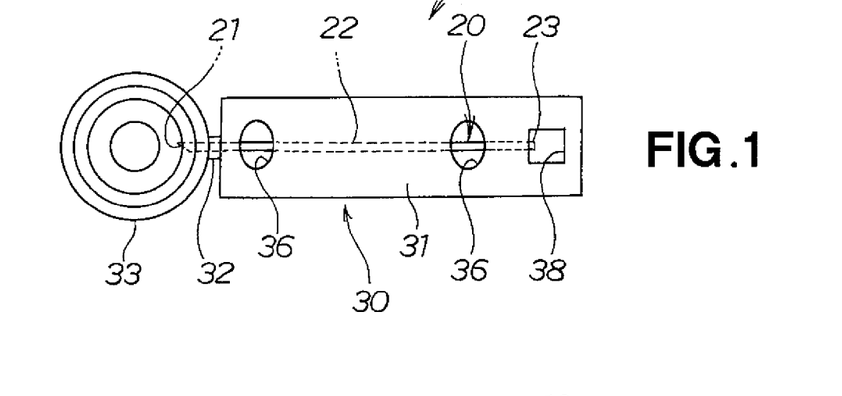
FIG. 1 is a plan view of an insert-molded product.
Figure 2:
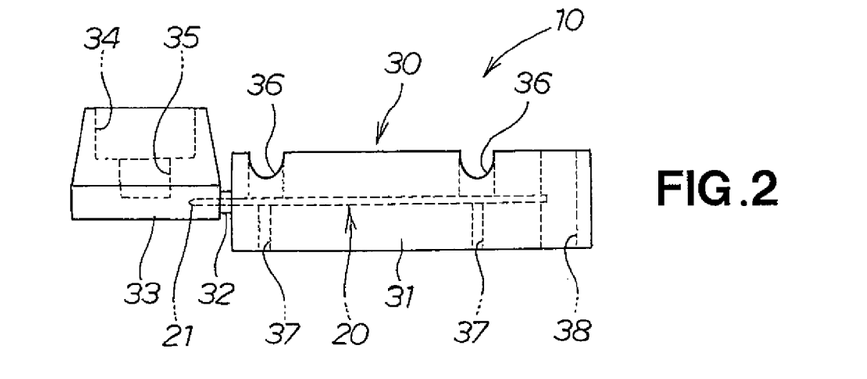
FIG. 2 is a side elevation view of the insert-molded product.

Referring to FIG. 1 and FIG. 2, an insert-molded product 10 includes a bar-shaped insert 10 and a resin 30 encapsulating the insert 10. The bar-shaped insert 10 has a pointed end and an end opposite the pointed end and having an end face lying in plane perpendicular to an axis of the product 10.

The insert-molded product 10 may be a puncture device. In this case, the insert 20 may be a blood collection needle 22 having a needle tip 21. The resin 30 includes a holder portion 31 encapsulating the needle 22 except for the tip 21. The tip 21 is encapsulated by a cap portion 33 of the resin 30. The cap portion 33 is connected to the holder portion 31 through a neck portion 32 of the resin 30.

Figure 3:
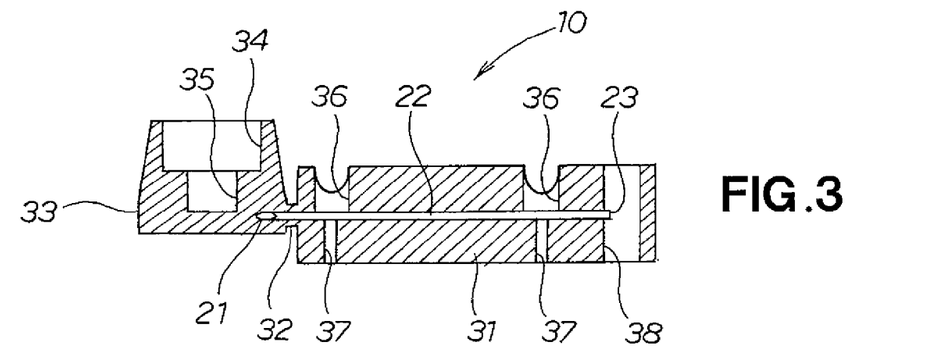
FIG. 3 is a cross-sectional view of the insert-molded product.

As shown in FIG. 3, the cap portion 33 includes an inlet defining a hole 34 of enlarged diameter. Provided behind the hole 34 is a hole 35 of reduced diameter. The hole 35 is smaller in diameter than the hole 34. The holder portion 31 has two V block holes 36, 36 spaced axially of the needle 22, and two pinholes 37, 37 provided in correspondence to the V block holes 36, 36. The holder portion 31 also has a though-hole 38 formed in a vicinity of an opposite end 23 of the needle 22 and extending perpendicularly to an axis of the needle 22.

Figure 4A:
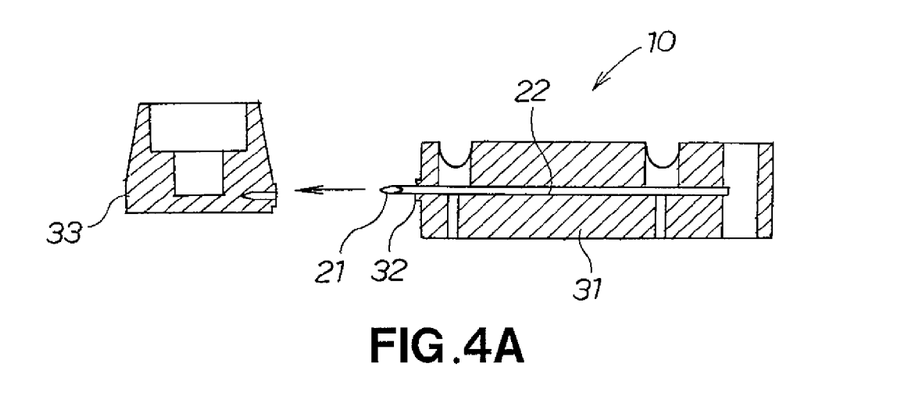
FIG. 4A is a cross-sectional view of the insert-molded product as the product has a cap portion twisted off for blood collection.
Figure 4B:
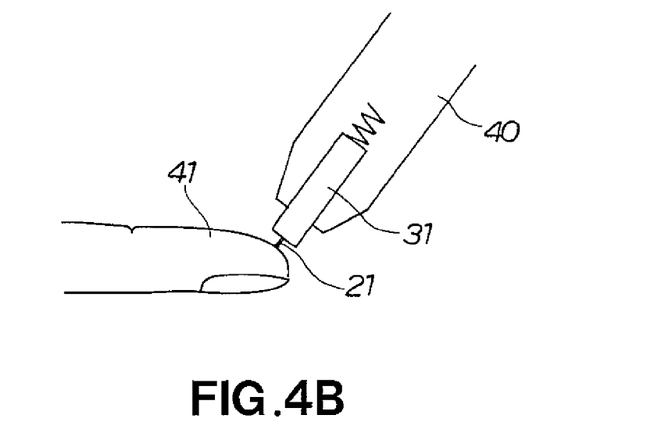
FIG. 4B is a view showing that a needle tip of a blood collection needle of the insert-molded product draws a drop of blood from a tip of a finger and FIG. 4C is a view showing that the needle tip of the blood collection needle is covered by a cap after drawing the drop of blood.
Figure 4C:
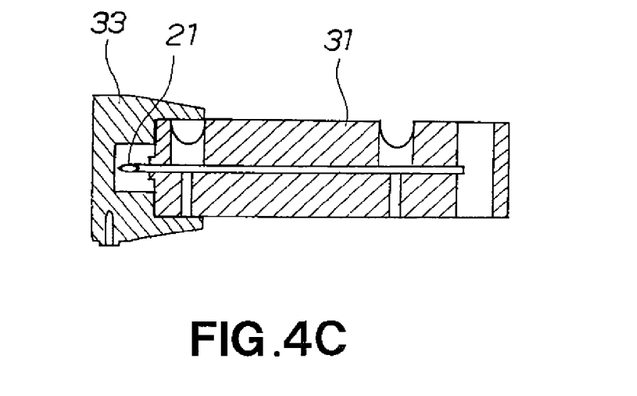

When the insert-molded product 10 is to be used, the cap portion 33 is twisted off cutting the neck portion 32, as shown in FIG. 4A, to expose the needle tip 21. The holder portion 31 is then set in an ejector 40, as shown in FIG. 4B. The ejector 40 ejects the holder portion 31 onto a tip 41 of a human finger, such that the needle tip 21 of the needle 22 draws a drop of blood from the tip 41 of the finger. The needle tip 21 may draw a drop of blood from a palm, an arm, an upper limb, a thigh or a calf. After drawing the drop of blood, the needle tip 21 of the needle 22 is covered by the cap portion 33, as shown in FIG. 4C.

Discussion will be made as to a mold 50 for producing the insert-molded product 10.

Figure 5:
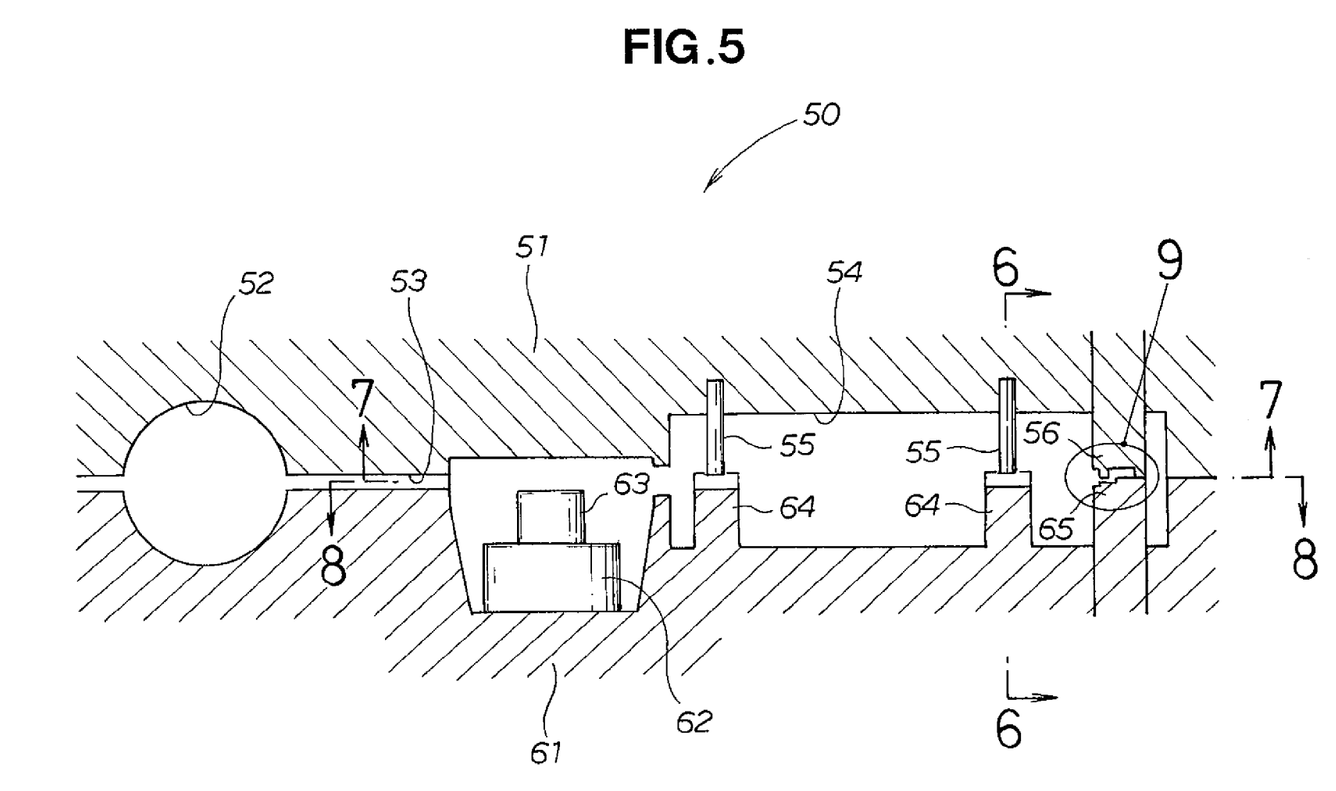
FIG. 5 is a cross-sectional view of a molded assembly for insert molding according to the present invention.

As shown in FIG. 5, the mold 50 includes an upper mold 51 and a lower mold 61. The upper mold 51 and the lower mold 61 define a runner 52, a gate 53 and a product cavity 54 therebetween.

The upper mold 51 includes pins 55, 55 for clamping an insert. Detachably attached to the upper mold 51 is an upper column 56. The detachable upper column 56 may be replaced with another one for various applications. In another embodiment, the upper column 56 may be integral with the upper mold 51.

The lower mold 52 includes a first projection 62 of enlarged diameter, a second projection 63 of reduced diameter, and two V block portions 64, 64. Detachably attached to the lower mold 61 is a lower column 65. In another embodiment, the lower column 65 may be integral with the lower mold 61. The number of the pins 55 and the number of the V block portions 64 may be three or more.

Figure 6:
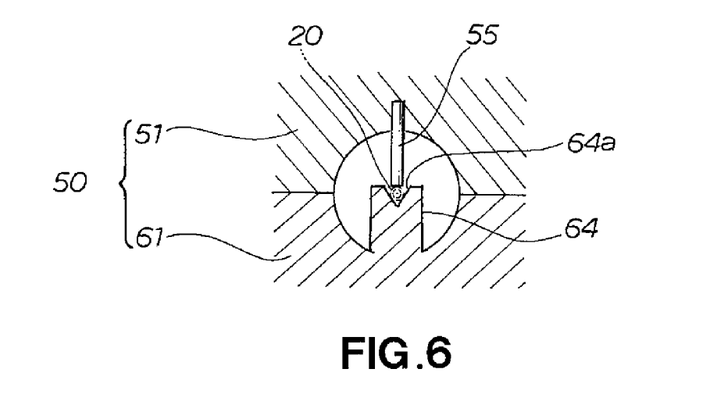
FIG. 6 is a cross-sectional view taken along line 6-6 of FIG. 5.

Turning to FIG. 6, the pin 55 clamps a cylindrical insert 20 shown by a phantom line as the insert 20 is placed within a V groove 64a formed on the V block portion 64. This holds the insert 20 in position to prevent the insert 20 from moving vertically and in a lateral direction parallel to the sheet of FIG. 6.

Figure 7:
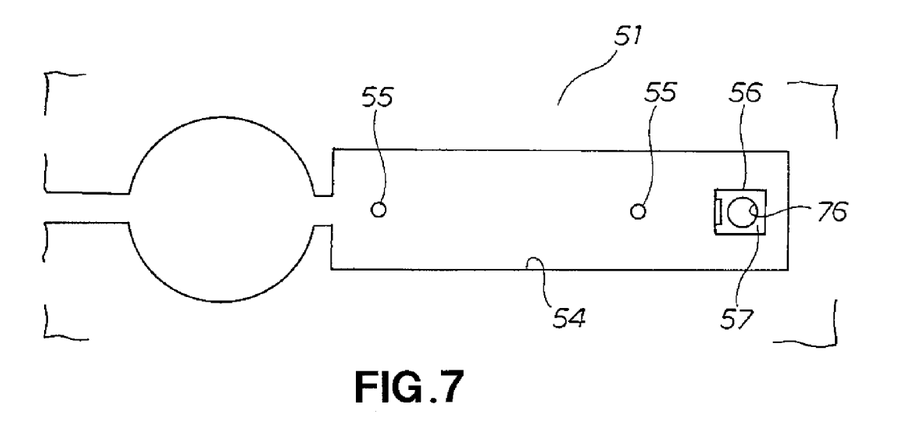
FIG. 7 is a view of the mold viewed in a direction of an arrow 7 of FIG. 5.

The upper column 56 is a quadrilateral prism having an end surface 57 (FIG. 7) machined as will be detailed later.

Figure 8:
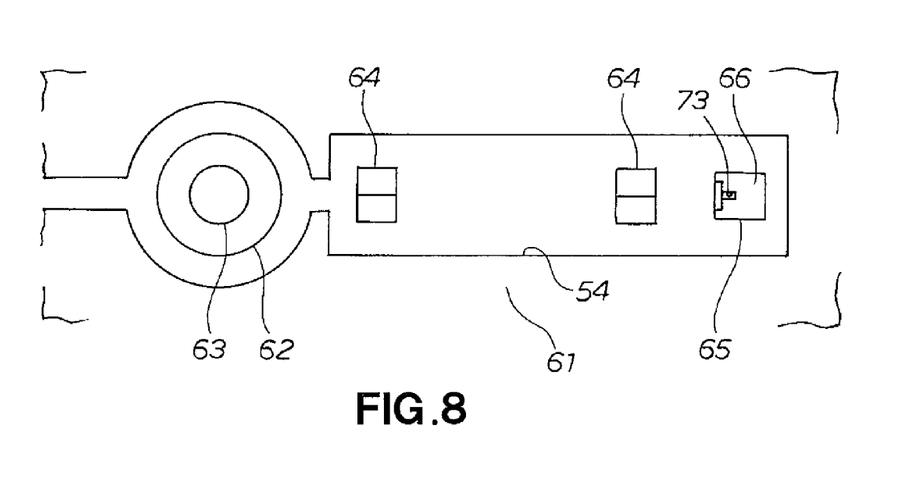
FIG. 8 is a view of the mold viewed in a direction of an arrow 8 of FIG. 5.

The lower column 65 is a quadrilateral prism having an end surface 66 (FIG. 8) for abutment on the end surface 57 of the upper column 56. The end surface 66 of the lower column 65 is machined as will be detailed later.

Figure 9:
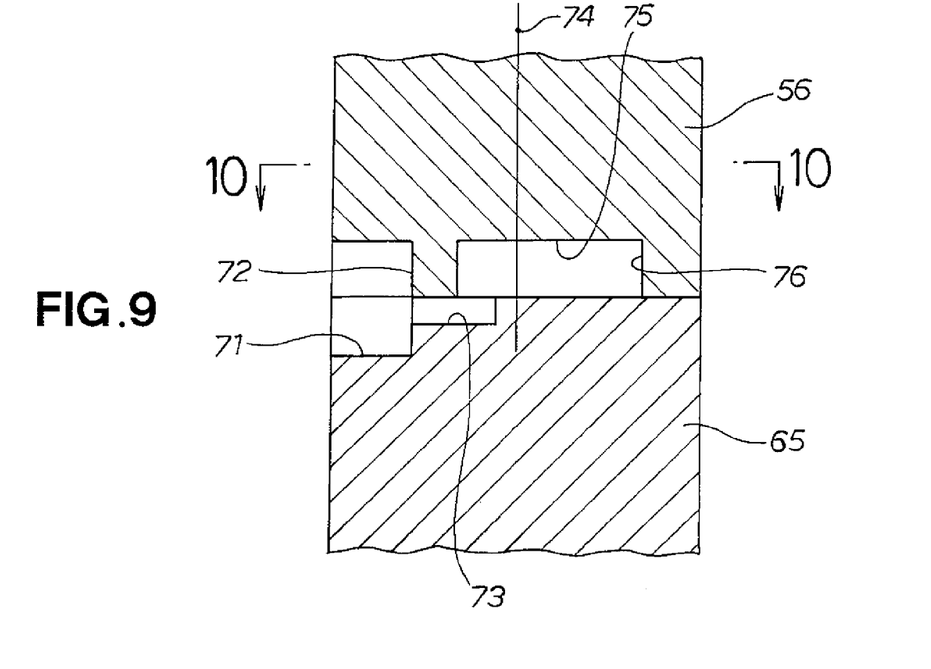
FIG. 9 is an enlarged view of a portion of the mold indicated by reference numeral 9 of FIG. 5.

As shown in FIG. 9, the upper column 56 and the lower column 65 define a recessed portion 71 for receiving the opposite end 23 (FIG. 3) of the insert 20. The recessed portion 71 has a back wall 72 for abutment on the end face of the opposite end of the insert. The back wall 72 has a resin passage portion 73 extending therethrough. The resin passage portion 73 has a cross-sectional area smaller than a cross-sectional area of the recessed portion 71. The upper column 56 defines a projection-forming cavity portion 76 communicating with an outlet port of the resin passage portion 73 for providing the insert-molded product with a projection (designated at 81 in FIG. 15). The cavity portion 76 has a surface 75 extending perpendicularly to an axis of the through-hole 38 or an axis 74 of the upper column 56. The surface 75 of the cavity portion 76 has an area larger than the cross-sectional area of the resin passage portion 73.

Figure 10:
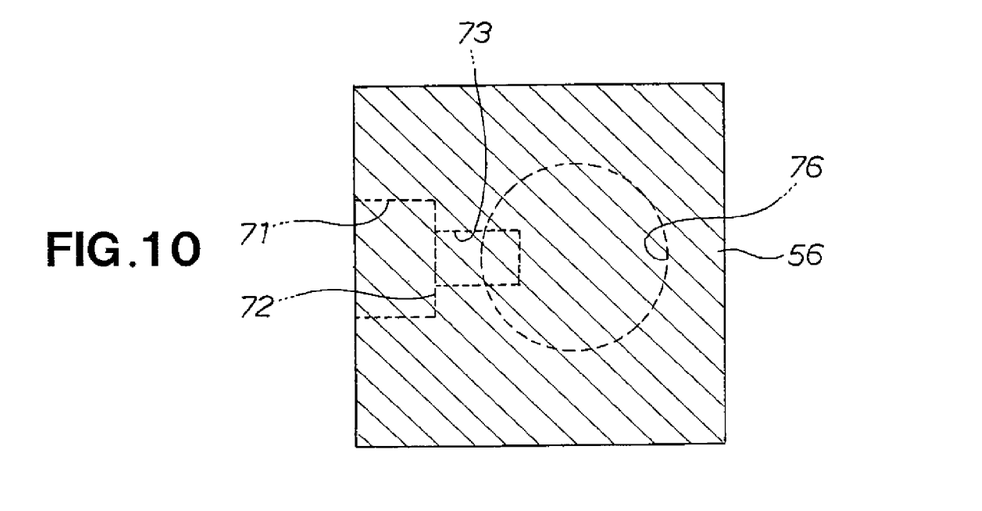
FIG. 10 is a cross-sectional view taken along line 10-10 of FIG. 9.

As shown in FIG. 10, the resin passage portion 73 has an inlet port communicating with the recessed portion 71 and the outlet port communicating with the projection-forming cavity portion 76. The cavity portion 76 is preferably formed proximate a center of the upper column 56.

Discussion will be made as to how the mold 50 produces an insert-molded product.

Figure 11:
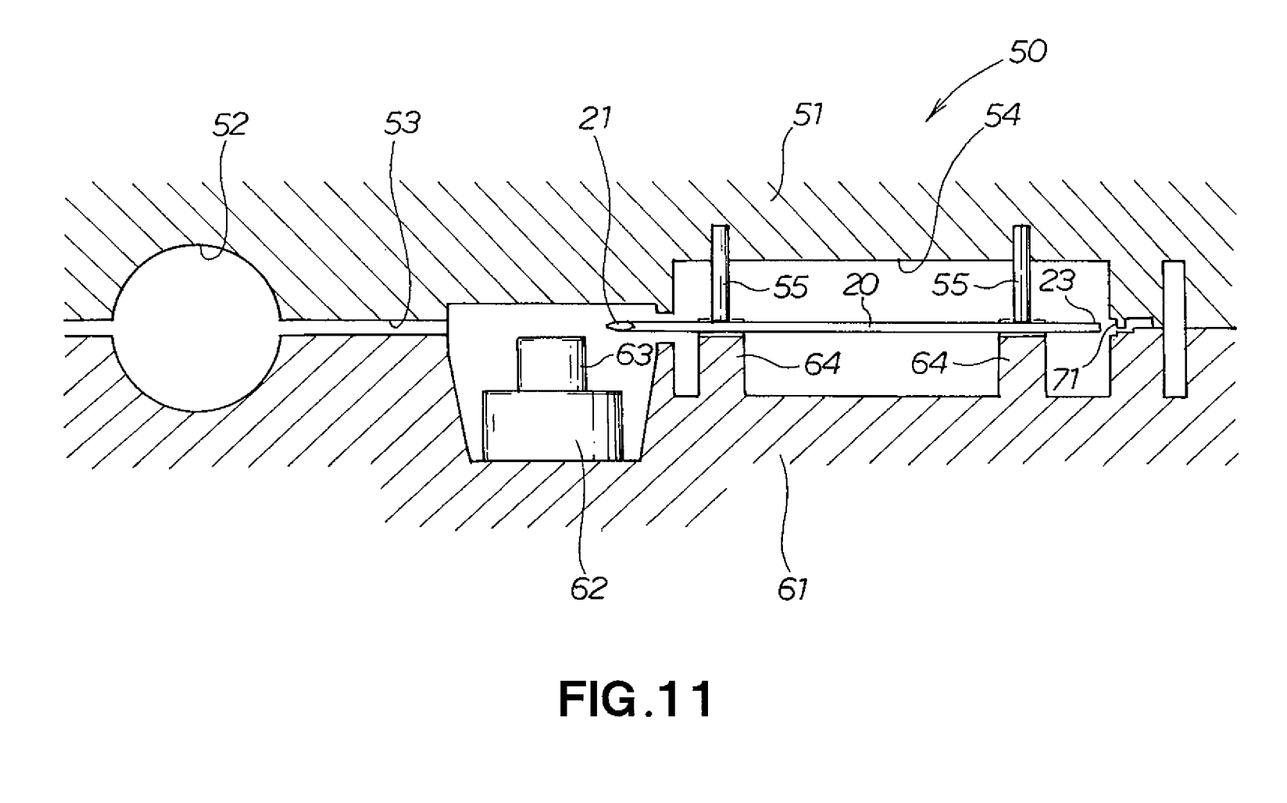
FIG. 11 is a cross-sectional view of the mold with an insert placed in the assembly for insert molding.

As shown in FIG. 11, an insert 20 is placed on the V block portions 64, 64 of the lower mold 61. The upper mold 51 is moved onto the lower mold 61 with the insert 20 placed on the V block portions 64, 64, such that the pins 55, 55 retain the insert 20 loosely on the V block portions 64, 64.

Figure 12:
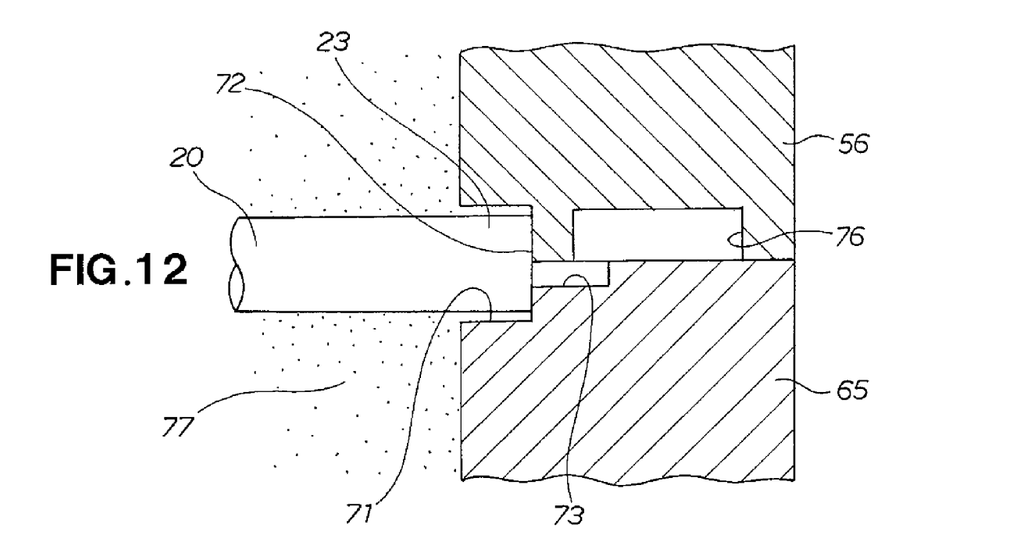
FIG. 12 is a view showing that an insert is disposed in correct orientation with an end of the insert being received in a recessed portion of the mold during insert molding.

Molten resin is injected through the runner 52 and the gate 53 into the product cavity 54. The pressure of the injected molten resin moves the insert 20 in a direction away from the gate 53. As a result, the opposite end 23 of the insert 20 moves into the recessed portion 71 to bring the end face of the opposite end 23 of the insert 20 into abutment on the back wall 72 of the recessed portion 71, as shown in FIG. 12. The end face of the opposite end 23, which extends perpendicularly to the axis of the insert 20, makes close contact with the back wall 72. The close contact between the end face of the opposite end of the insert and the back wall 72 seals the inlet port of the resin passage portion 73 to prevent resin 77 from entering the resin passage portion 73.

The above process discussed with reference to FIG. 11 and FIG. 12 results in producing the insert-molded product 10 explained with reference to FIG. 1 to FIG. 3. The insert-molded product 10 is inspected in a manner as will be discussed below with reference to FIG. 13.

Figure 13:
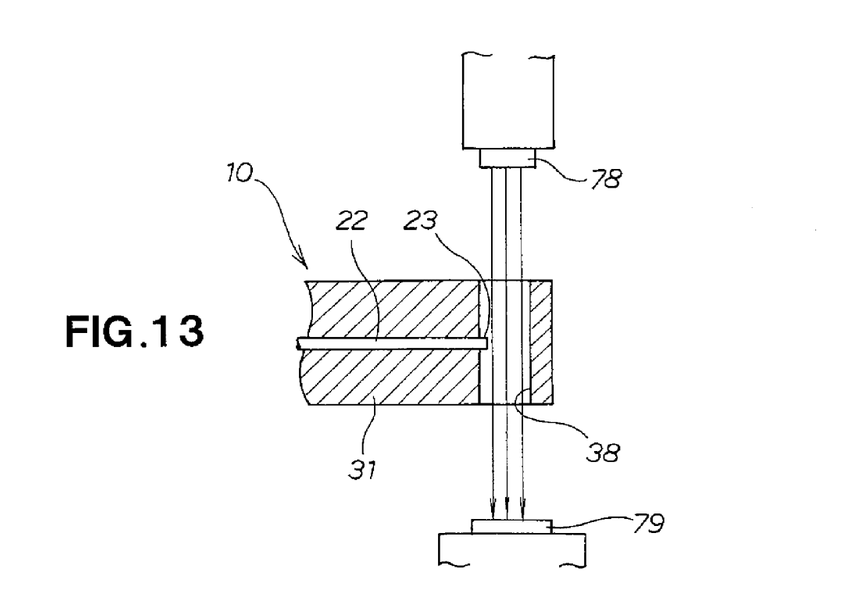
FIG. 13 is a view showing that an insert-molded product having the insert disposed in the correct orientation is inspected and judged to be acceptable.

As shown in FIG. 13, a light-emitting element 78 is disposed above the through-hole 38 of the insert-molded product 10 while a photodetector 79 is disposed below the through-hole 38. The element 78 may disposed below the through-hole 38 while the photodetector 79 may disposed above the through-hole 38. In another embodiment, the light-emitting element 78 and the photodetector 79 may be arranged in such a manner as to allow the element 78 to emit a light horizontally.

The light-emitting element 78 emits an infrared light or laser beam toward the photodetector 79. The emitted infrared light or laser beam is detected by the photodetector 79 after passing through the through-hole 38. If intensity or level of the infrared light or laser beam detected by the photodetector 79 is more than a predetermined value, the insert-molded product 10 is judged to be acceptable.

The light-emitting element 78 and the photodetector 79 are optical sensors of non-contact type. These optical sensors have so high a sensing speed that they inspect the insert-molded product in a shorter time than contact-type sensors. The optical sensors may have a function of image sensors to conduct image analysis for detecting an area of the through-hole 38. Based on the area of the through-hole 38, the sensors may judge whether the insert-molded product is acceptable or rejected. It is to be noted that any non-contact type of optical sensors other than those optical sensors may be used for inspection of the insert-molded product 10.

Discussion will be made as to an insert-molded product rejected due to wrong orientation or irregular deformation of the insert 20.

Figure 14:
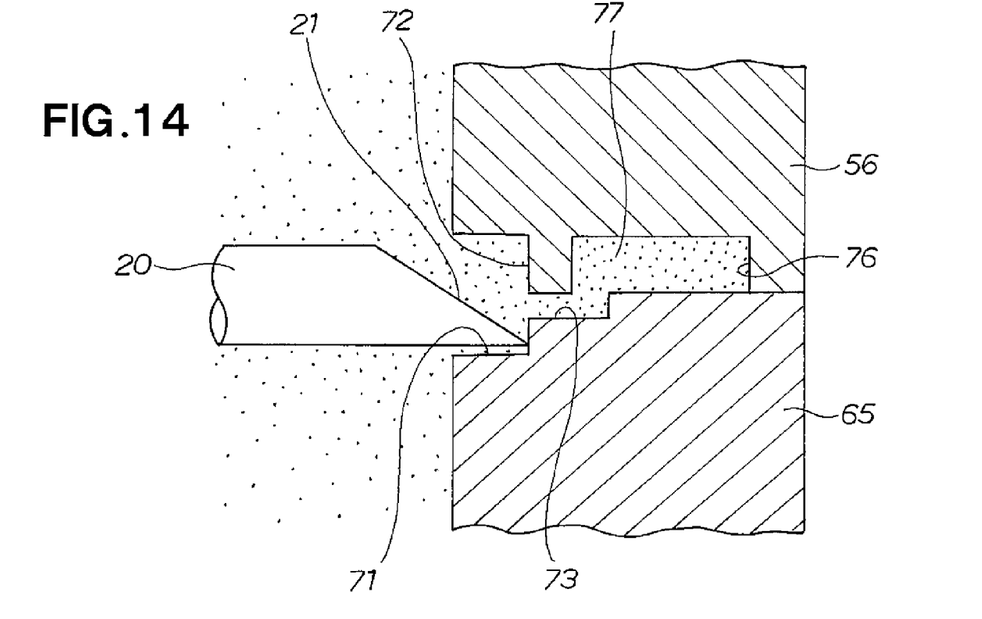
FIG. 14 is a view showing that an insert is disposed in wrong orientation with a pointed end of the insert being received in the recessed portion of the mold during insert molding.
Figure 15:
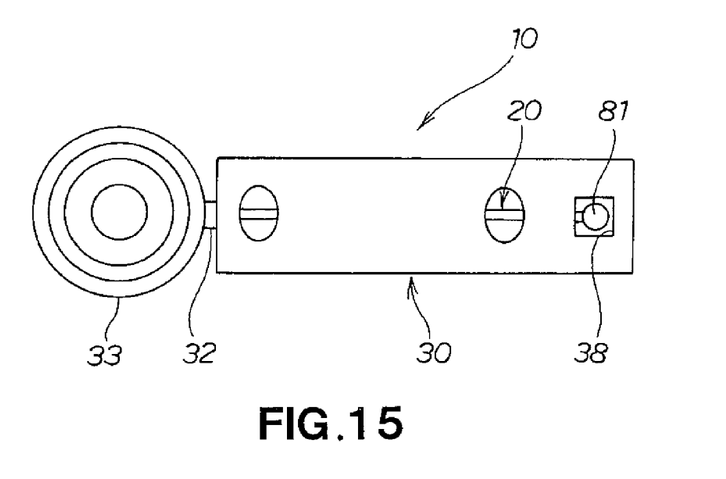
FIG. 15 is a plan view of an insert-molded product including a projection.

As shown in FIG. 14, when a needle tip 21 of the insert 20 is received in the recessed portion 71 abutting on the back wall 72, the inlet port of the resin passage portion 73 remains open. With the inlet port opened, resin 77 fills the projection-forming cavity portion 76 after passing through the resin passage portion 73. The resin 77, which has filled the cavity portion 76, is solidified into a projection 81, as shown in FIG. 15. That is, the projection 81 is formed by the projection-forming cavity portion 76. The projection 81 is located substantially in the middle of the through-hole 38 when the upper and lower columns 56, 65 move away from each other.

Figure 16:
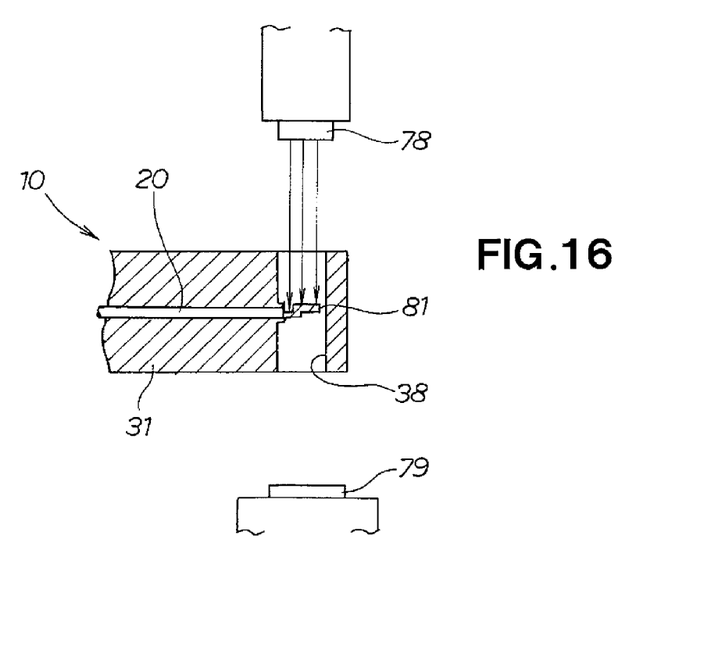
FIG. 16 is a view showing that the insert-molded product including the projection is inspected and judged to be rejected.

As illustrated in FIG. 16, the projection 81 blocks most of infrared light or laser beam emitted from the light-emitting element 78. As a result, the photodetector 79 detects the emitted infrared light or laser beam having intensity less than the predetermined value. Such an insert-molded product 10 having the projection 81 is judged to be rejected.

The light-emitting element 78 may be a readily available diode that emits an infrared light or laser beam, and there are no specific restrictions on use of such a diode.

The light-emitting element 78 and the photodetector 79 have improved ability to effect rapid inspection of the insert-molded product. It is to be noted that the insert-molded product may be visually inspected when the product is produced in small amounts.

The use of the optical sensors or the visual inspection makes it possible to judge that the insert-molded product is rejected if the through-hole is closed and the insert-molded product is acceptable if the through-hole is not closed. The use of the optical sensors or the visual inspection enables easy inspection of the insert-molded product without requiring any X-ray inspection device or radiological technologists.

Figure 17A:
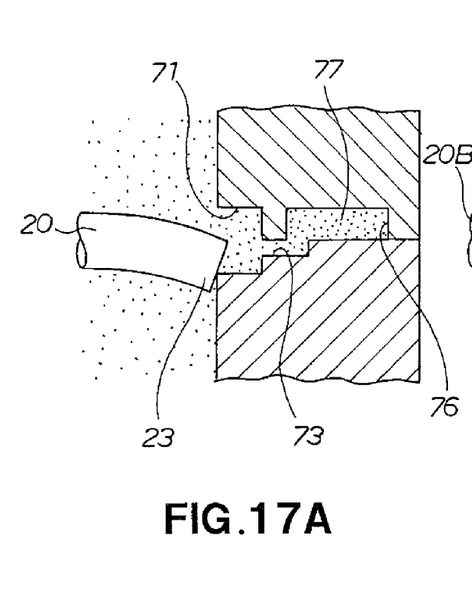
FIG. 17A and FIG. 17B are views showing insert-molded products judged to be rejected.

The resin passage portion 73 can be opened not only when the needle tip is received within the recessed portion 71 as discussed above, but also when the insert 20 is bent so that the opposite end 23 is not received within the recessed portion 71, as shown in FIG. 17A. As the opposite end 23 is not received within the recessed portion 71, as shown in FIG. 17A, resin 77 fills the projection-forming cavity portion 76 after flowing through the open resin passage portion 73.

Figure 17B:
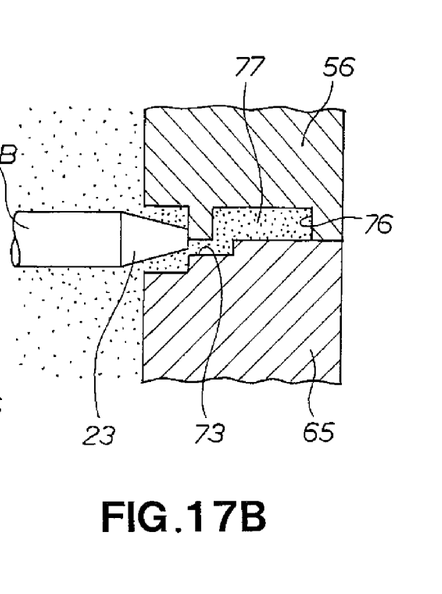

The resin passage portion 73 can be also open when a wrong type of an insert 20B having a conical projection is set within the recessed portion 71, as shown in FIG. 17B. As a result, resin 77 fills the projection-forming cavity portion 76 after passing through the open resin passage portion 73.

Although not shown, the resin passage portion 73 can be also open when there is no insert. In this case, resin 77 fills the projection-forming cavity portion 76 after passing through the open resin passage portion 73.

The mold according to the present invention can detect wrong orientation or irregular deformation of the insert 20, placement of wrong type of the insert, and absence of an insert.

Figure 18A:
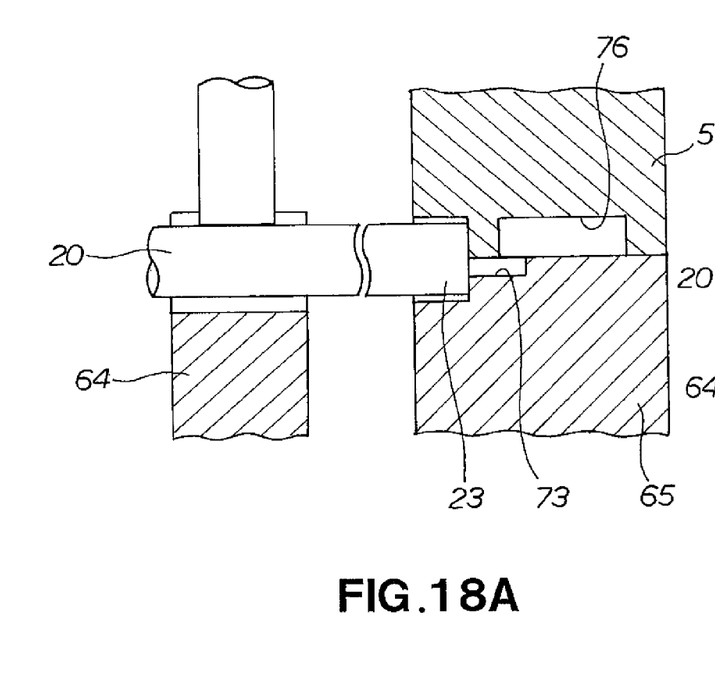
FIG. 18A and FIG. 18B are views showing that inserts having different outer diameters are placed in the mold according to the present invention.
Figure 18B:
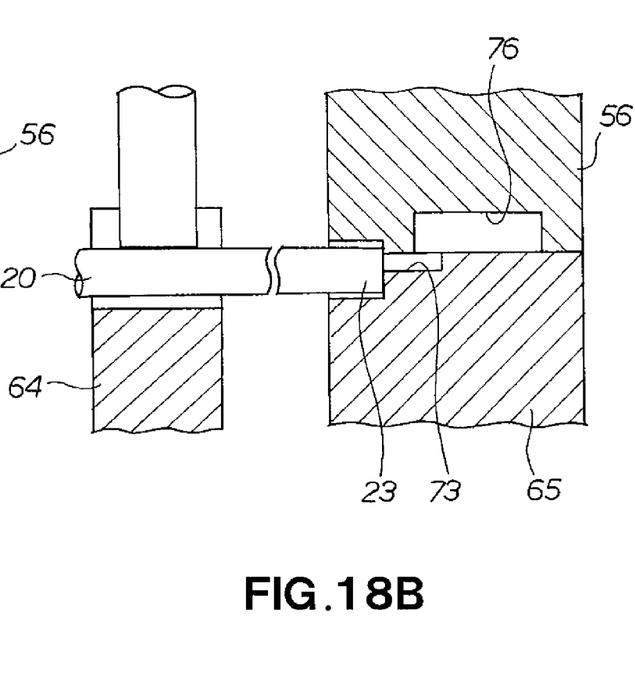

FIG. 18A shows an insert 20, a blood collection needle having an outer diameter of 0.5 mm. FIG. 18B shows an insert 20, a blood collection needle having an outer diameter of 0.3 mm. The V block portion 64 cooperates with the pin 55 to position the insert 20 in such a manner as to prevent the insert 20 from shifting laterally (in a direction perpendicular to the sheet of FIG. 18A and FIG. 18B) regardless of whether the outer diameter of the insert 20 is 0.5 or 0.3 mm.

The resin passage portion 73 is defined by the lower column 65 in such a manner as to be closed by the opposite end 23 of the insert 20 regardless of the outer diameter of the insert 20. The lower column 65, which defines the resin passage portion 73, shares the insert 20 with the lower die regardless of the outer diameter of the insert 20.

Figure 19:
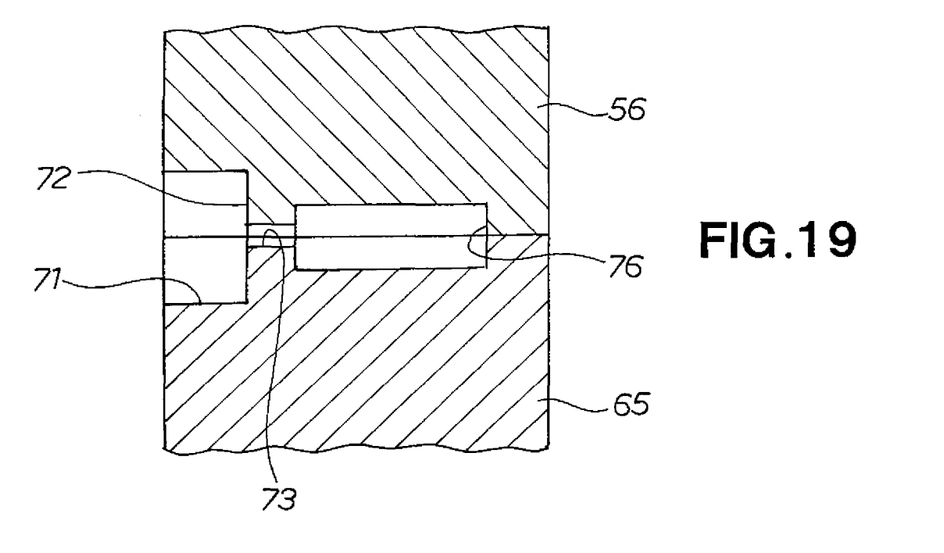
FIG. 19 is a view showing modification to the portion of the mold shown in FIG. 9.

The recessed portion 71, the resin passage portion 73 and the projection-forming cavity portion 76 all have upper halves defined by the upper column 56 and lower halves defined by the lower column 65, as shown in FIG. 19. The upper and lower columns 56, 65 defining those upper and lower halves are easy to design.

Figure 20:
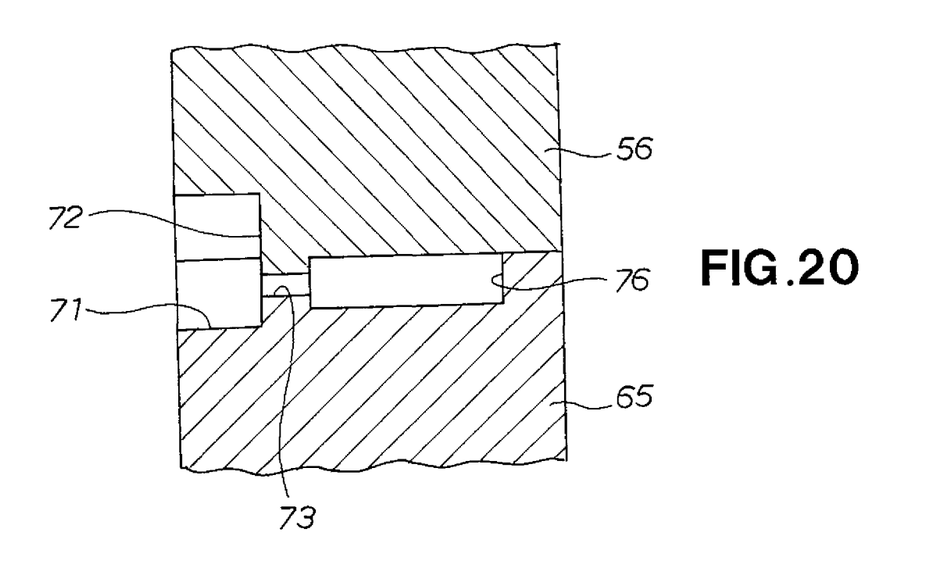
FIG. 20 is a view showing further modification to the portion of the mold shown in FIG. 9.

The lower column 65 may define the resin passage portion 73 and the projection-forming cavity portion 76, as shown in FIG. 20. In this case, the upper column 56 can be subjected to a reduced number of machining operations because the upper column 56 is not required to define the resin passage portion 73 and the cavity portion 76.

The mold according to the present invention is applicable to producing another type of puncture device by insert molding.

Figure 21:
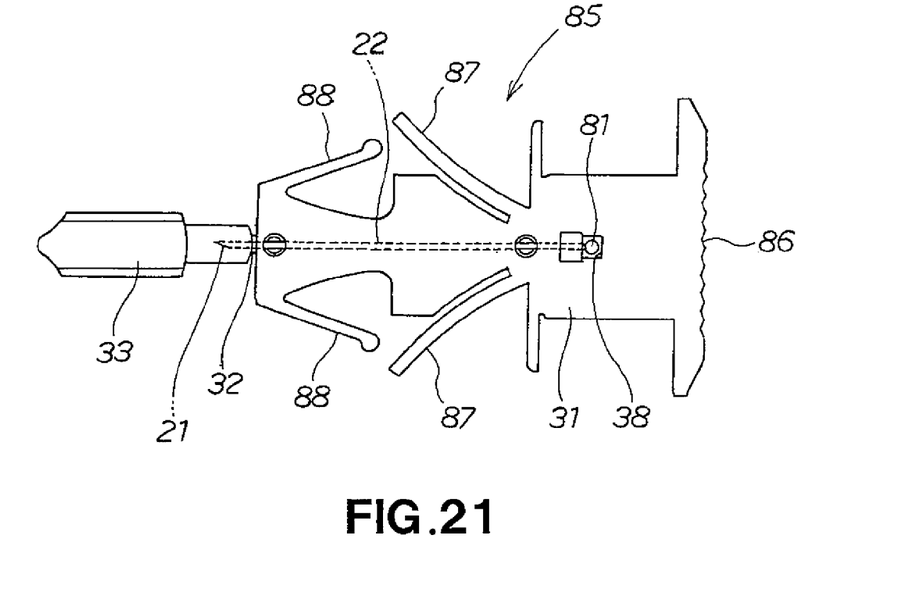
FIG. 21 is a view showing a modified insert-molded product.

As shown in FIG. 21, a puncture device 85 includes a blood collection needle 22. The needle 22 has a pointed needle tip 21 encapsulated by a cap portion 33 of the device 85. The remaining part of the needle 22 is encapsulated by a holder portion 31 of the device 85. The holder portion 31 is connected to the cap portion 33 through a neck portion 32 of the device 85. The holder portion 31, the neck portion 32 and the cap portion 33 are molded integrally with one another.

The holder portion 31 includes an engagement portion 86 for engagement with fingers of a user when the holder portion 31 is to move to an advanced position, spring portions 87, 87 for moving the holder portion 31 back to a retracted position after the holder portion 31 has been advanced or used, and stopper portions 88 for preventing the holder portion 31 from moving again from the retracted position to the advanced position.

The holder portion 31 defines a through-hole 38 in a vicinity of the opposite end 23 of the needle 22.

If the needle 22 is disposed in wrong orientation with the needle tip 21 in a position opposite the position shown in FIG. 21, a puncture device has a projection 81 formed within the through-hole 38. Such a puncture device is judged to be rejected.

The presence of the projection 81 results in detection of abnormal conditions such as wrong orientation or irregular deformation of the needle 22 and a wrong type of a needle, etc.

The shape of the projection 81 is not limited to the circular one, but includes other ones such as an oval, a triangle, a rectangle and a polygon, as viewed in top plan. The cross-sectional shape of the through-hole is not limited to a rectangle, but includes other shapes such as a circle, an oval and polygon other than a quadrangle.

The insert-molded product is not limited to that shown in FIG. 1 to FIG. 3, but includes any type of products having resin and inserts all or most of which are encapsulated by resin.

The insert is not limited to the blood collection needle, but includes a wire or a rod.

The mold according to the present invention is suitable for producing an insert-molded puncture device for blood collection.

Obviously, various minor changes and modifications of the present invention are possible in light of the above teaching. It is therefore to be understood that within the scope of the appended claims the invention may be practiced otherwise than as specifically described.

What is claimed is:

1. A mold for insert molding, the mold having a product cavity configured such that molten resin is injected into the product cavity with a bar-shaped insert set in the product cavity so as to produce an insert-molded product including a resin and the insert encapsulated by the resin, the insert has a pointed end and an end opposite the pointed end, the opposite end of the insert having an end face lying in a plane perpendicular to an axis of the product, the mold comprising:
    an upper mold;
    a lower mold; and
    a pair of columns including an upper column integral with or releasably attached to the upper mold and a lower column integral with or releasably attached to the lower mold, the upper column and the lower column projecting into the product cavity toward the opposite end of the insert, the upper column and the lower column being configured to jointly form a through-hole extending through the insert-molded product in a direction perpendicular to an axis of the insert,
    the pair of columns jointly including:
        a recessed portion for receiving the opposite end of the insert, the recessed portion having a back wall for abutting on the end face of the opposite end of the insert received in the recessed portion;
        a resin passage portion extending through the back wall and having a cross-sectional area smaller than a cross-sectional area of the recessed portion; and
        a projection-forming cavity portion communicating with an outlet port of the resin passage portion for providing the insert-molded product with a projection, the projection-forming cavity portion including a surface extending perpendicularly to an axis of the through-hole and having an area larger than the cross-sectional area of the resin passage portion.

2. The mold of claim 1 wherein the insert is a blood collection needle.

* * * * *